United States Patent [19]
Ikeda et al.

[11] Patent Number: 6,155,096
[45] Date of Patent: Dec. 5, 2000

[54] LIGHT TRANSMISSION TYPE POWDER AND GRANULAR MATERIAL MEASURING APPARATUS

[75] Inventors: Hideyuki Ikeda, Nishikyo-ku; Yasushi Watanabe, Numazu; Kiyoshi Morimoto, Mishima; Satoru Hiruta, Sunto-gun, all of Japan

[73] Assignees: Horiba, Ltd., Kyoto; Kyowa Hakko Kogyo Co., Ltd., Tokyo, both of Japan

[21] Appl. No.: 09/161,142

[22] Filed: Sep. 25, 1998

[30] Foreign Application Priority Data

Sep. 30, 1997 [JP] Japan ................................ 9-284479

[51] Int. Cl.$^7$ ................................................ G01N 1/00
[52] U.S. Cl. .............................................. 73/1.07; 73/1.88
[58] Field of Search ........................ 73/865.8, 1.01–1.03, 73/1.06, 1.07, 1.16, 1.34, 1.88; 356/243.1, 243.2, 441, 442, 438

[56] References Cited

U.S. PATENT DOCUMENTS

| | | | |
|---|---|---|---|
| 3,148,527 | 9/1964 | Lindquist et al. | 73/1.34 |
| 3,867,835 | 2/1975 | Button | 356/243.2 |
| 3,885,162 | 5/1975 | Geertz | 356/243.2 |
| 3,994,601 | 11/1976 | Brugger | 356/243.2 |
| 3,997,271 | 12/1976 | Brugger et al. | 356/243.2 |
| 4,384,925 | 5/1983 | Stetter et al. | 73/1.07 |
| 5,261,285 | 11/1993 | Tokoyama | |
| 5,421,188 | 6/1995 | Sager | 73/1.34 |
| 5,597,949 | 1/1997 | Kalotay | 73/1.03 |
| 5,648,605 | 7/1997 | Takahashi | 73/1.35 |

FOREIGN PATENT DOCUMENTS 2198525  6/1988  United Kingdom.

*Primary Examiner*—Robert Raevis
*Attorney, Agent, or Firm*—Price, Gess & Ubell

[57] ABSTRACT

A light transmission powder and granular material measuring apparatus for a continuous production line assembly is provided. A conduit line is capable of being connected to the production line to provide an alternative flow path for the powder and/or granular material. A light transmission cell is mounted in the conduit and a measurement apparatus is provided for measuring the light as it passes through the light transmission cell. A valve member can interconnect the conduit to the production line to control the flow of powder and/or granular material, whereby a measurement can be made when the valve is activated to permit the flow of powder and/or granular material to provide an accurate measurement, and also a measurement can be made as a reference measurement during a calibration cycle when the valve is activated to stop the flow of powder and/or granular material. The light transmission powder and/or granular material measuring apparatus can be provided as a modular unit for mounting in a continuous production line and can be automatically controlled to periodically calibrate its measurements.

8 Claims, 5 Drawing Sheets

FIG. I

LIGHT TRANSMISSION TYPE POWDER AND GRANULAR MATERIAL MEASURING APPARATUS

BACKGROUND OF THE INVENTION

1. Field of the Invention

The present invention relates to a light transmission type powder and granular material measuring apparatus and more particularly to a modular system that can be added as a measuring line to a continuous production line.

2. Description of Related Art

Light transmission powder and granular material measuring apparatus in which the powder and granular materials flow through a cell equipped with a glass window on both sides to be irradiated with a laser beam, e.g., through one glass window and with the light transmitted to the other glass window to be detected are well known. Based on the characteristics of the laser beam transmittance, the concentration and particle size distribution of the powder and granular material can be determined. However, any powder and granular material adhering to the cell window can lower the light transmittance and can affect the measurement of powder and granular material.

Therefore, in order to correctly measure an altered value due to the cloudiness of the glass window, light transmittance was measured when powder and granular material was not permitted to flow in the cell (blank or reference measurement), and with this blank measurement designated as a blank value, the blank value was subtracted from the actual measured value when the powder and granular material was allowed to flow. Therefore, the lowering of the measured value due to any cloudiness of the glass window was corrected and error was reduced.

However, in the above-mentioned light transmission powder and granular material measuring apparatus, the flow of the powder and granular material along a production line conduit to which the cell was connected must be stopped temporarily in order to carry out a blank measurement. Consequently, when the concentration and particle size distribution of powder and granular material flowing in the plant line was measured by a light transmission type powder and granular material measuring apparatus as described above, the line of the plant must be temporarily stopped during the blank measurement every time the blank measurement was carried out, and it has been generally unable to use such a light transmission type powder and granular material measuring apparatus as described above, in those plants where the line must be constantly operated.

Constantly, hitherto, a light transmission type powder and granular material measuring apparatus was generally not used for measuring the blank valve in a plant line, and in many cases, supervisors of plant lines had to control the product quality by their own experience accumulated over many years.

OBJECTS AND SUMMARY OF THE INVENTION

In view of the foregoing, it is an object of this invention to provide a light transmission type powder and granular measuring apparatus and system, which can carry out a blank or reference measurement without stopping the flow of the powder and granular material inside the line. In order to achieve the above object, a modular unit of a light transmission type powder and granular measuring apparatus according to this invention can comprise two segments or pieces of piping or conduits connected in such a manner to branch the powder and granular material flowing line into two separate paths at a divergence point and to join the flow again at a confluence point. A valve is installed at the divergence point and can be changed over to allow the powder and granular material to selectively flow in either one of the piping, while a light transmission type cell is mounted in at least one of the piping, wherein both a condition in which the powder and granular material is allowed to flow in the cell and a condition in which the powder and granular material is not allowed to flow in the cell can be measured by changing over the valve without stopping the flow of the powder and granular material.

Consequently, because the flow of the powder and granular material with respect to the piping to which the cell of the light type powder and granular measuring apparatus is connected is stopped and a blank or a reference measurement is carried out, and simultaneously it is possible to allow the powder and granular material to flow in another piping branch connected to the production line, the powder and granular material flowing in the line can be allowed to constantly flow without stopping. That is, even in a production plant in which the line flow is unable to be stopped, a light transmission type powder and granular material measuring apparatus can be installed on the production line, and high-accuracy processing can be achieved.

When a valve is installed in the space from the confluence point to the cell, it is possible to remove the cell from the piping for maintenance with the valve changed over to prevent powder and granular material from flowing to the cell. Consequently, the accuracy of the light transmission type powder and granular material measuring apparatus can be further improved by removing the powder and granular material adhering to the glass window.

In addition, when a light transmission type cell is installed in both of the two pieces of piping, respectively, while blank measurement or maintenance is being carried out with one cell, the concentration measurement and particle size distribution measurement of the powder and granular material can be continuously carried out with the other cell, making it possible to constantly and accurately control the powder and granular material flowing in the plant line, while frequent calibration can be accomplished.

Using the blank or reference value measured by the above method, it becomes possible to get rid of the influence of cloudiness of the glass window on the measured signals and to reduce errors by subtracting the blank value when the sample is not allowed to flow in the piping from the measurement value when the sample is allowed to flow in the piping.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DETAILED DESCRIPTION OF THE PREFERRED EMBODIMENTS

Figure 1:
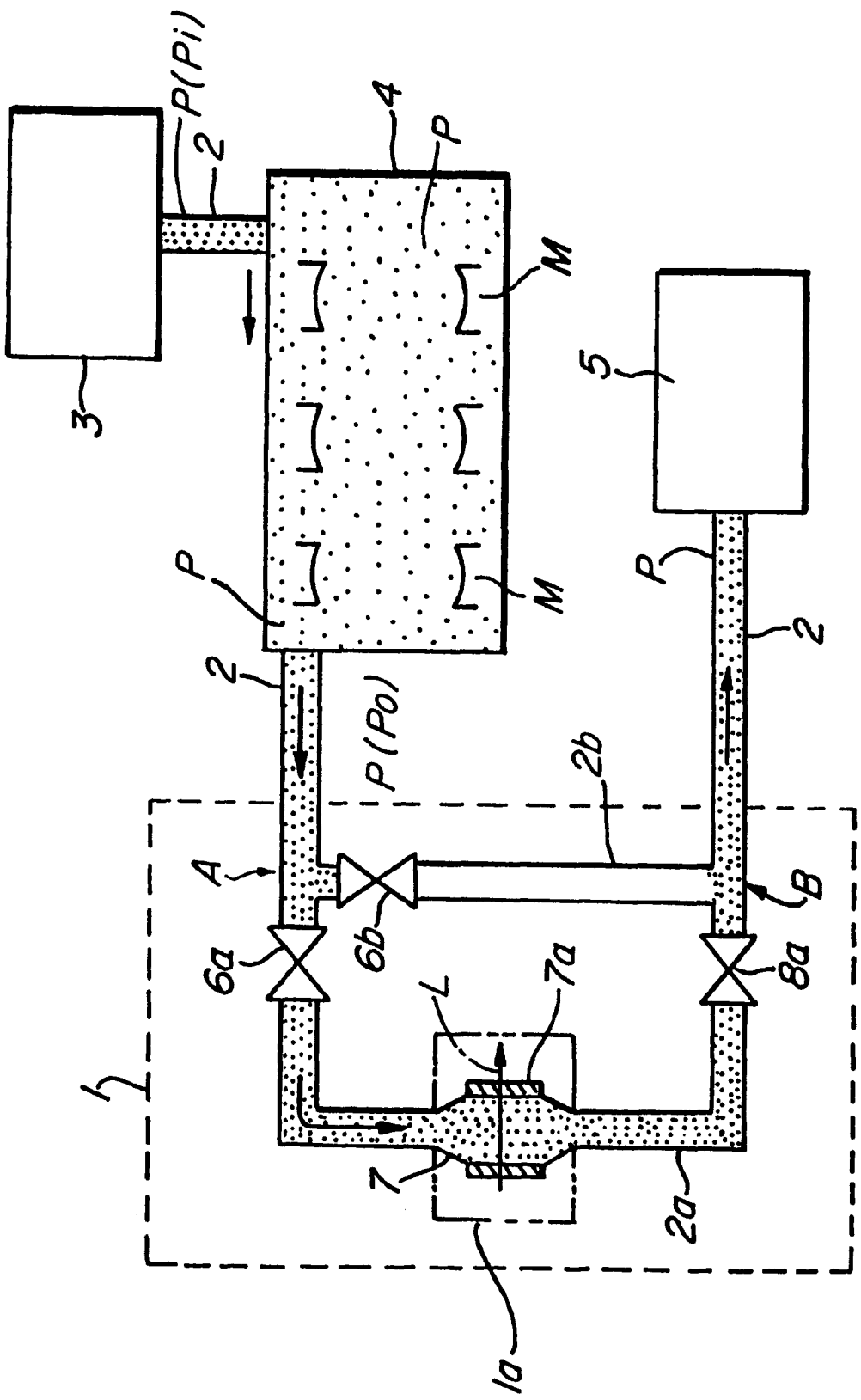
FIG. 1 is a drawing showing one example of a plant line using the light transmission type powder and granular material measuring apparatus according to this invention.

The following description is provided to enable any person skilled in the art to make and use the invention and sets forth the best modes contemplated by the inventors of carrying out their invention. Various modifications, however, will remain readily apparent to those skilled in the art, since the general principles of the present invention have been defined herein specifically to provide a light transmission powder and granular material measuring apparatus and system for a continuous production line.

Referring now to the drawings, the preferred embodiments according to the invention will be described in detail hereinafter.

Figure 2:
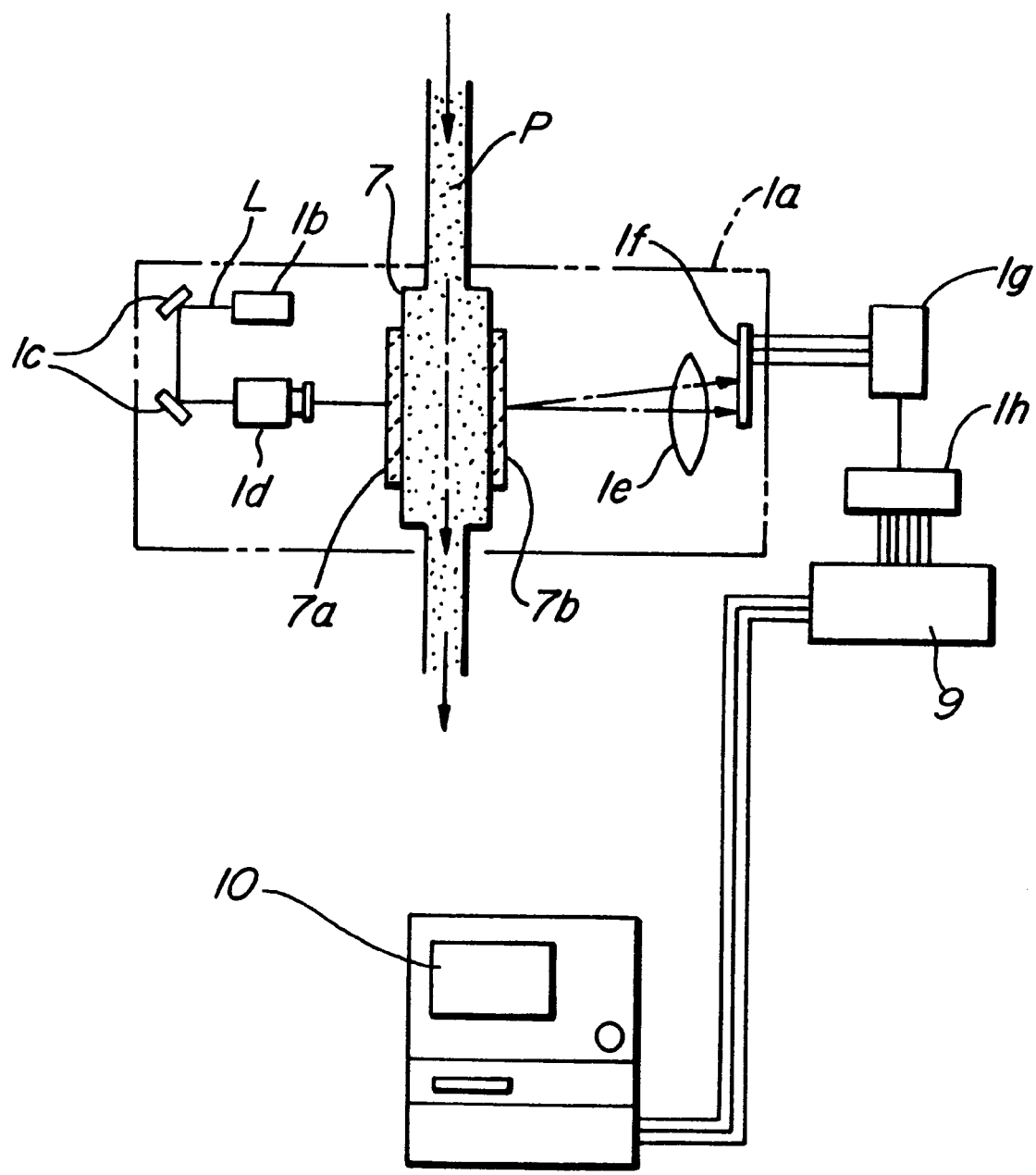
FIG. 2 is a block diagram showing a part of the light transmission type powder and granular material measuring apparatus.

FIG. 1 and FIG. 2 show one example of a light transmission type powder and granular material measuring apparatus according to this invention. In these drawings, numeral 1 is a light transmission type powder and granular material measuring apparatus module, and numeral 2 is a plant line in which this light transmission type granular and powder material measuring apparatus 1 can be installed.

The example shown in FIG. 2 indicates a line 2 conveying powder and granular material using air and other carrier gases, such as, for example, a line in a pharmaceutical plant for generating granular chemicals. On the upstream end of line 2, a powder and granular material transporting apparatus 3 is installed, which agitates the powder and granular material P comprising, for example, lubricants 15 $\mu$m in diameter with air and delivers them to line 2. Numeral 4 is a tablet compression molding machine for spraying the powder and granular material P delivered from the powder and granular material transporting apparatus 3 to the forming dies M and compressing the material into tablets. Numeral 5 is an aspirator for sucking excess powder and granular material P generated at the tablet compression molding machine 4 to remove them.

Line 2 is connected to module 1 in such a manner as to be branched into two flow paths at the diverging point A by two pieces of piping 2a, 2b, and which are joined into one again at the converging point B, and at this diverging point A, two valves 6a, 6b are installed to selectively connect either one of the two pieces of piping 2a, 2b. That is, the valve 6a becomes an open state when the valve 6b is in the closed position, and the valve 6a becomes a closed state when the valve 6b is in the open position. The valves 6a, 6b may be replaced by one three-way valve (not shown).

To one piping 2a, a light transmission type cell 7 is connected at a midway position, and to the converging point 8 on the downstream side, a valve 8a which acts in the same manner as the valve 6a of the diverging point A is connected. Consequently, by switching the valves 6a, 6b, and 8a, powder and granular material P flowing in line 2 can be switched either to flow in piping 2a or in piping 2b. That is, without completely affecting the flow of the powder and granular material P on line 2, the powder and granular material P can be optionally allowed to flow or stopped for the cell 7.

FIG. 2 is a sketch showing the configuration of the analysis section of the light transmission type powder and granular material measuring apparatus 1. In FIG. 2, numeral 1a designates an optical chamber, and in the optical chamber 1a, for example, a He—Ne laser 1b is installed, and a glass window 7a is irradiated with the laser beam L via reflection mirrors 1c, 1d, and a beam expander 1d. Numeral 1e is a condensing lens mounted opposite the glass window 7b of the cell 7.

Numeral 1f is a photo detector for detecting the light penetrating the cell 7 and passing through the glass window 7b, and comprising, for example, photo diodes arranged in a ring form to measure both direct light transmission and scattered light transmission. The transmittance data and scattering data which this photo detector 1f detects is intended to be inputted to a controller 9 via a multiplexer 1g and an A/D converter 1h. Number 10 is a display processing section, which displays the concentration and particle size distribution measured based on the detection data.

Now, a description is made on the operation of line 2 in a light transmission type powder and granular material measuring equipment 1 of the above configuration and a pharmaceutical plant with the light transmission type powder and granular material measuring equipment 1 installed.

The powder and granular material P delivered from the powder and granular material transporting apparatus 3 is sprayed into the forming dies M in the tablet compression molding machine 4, and any excess powder and granular material Po is discharged by being sucked by an aspirator 5 via the line 2.

Under the condition shown in FIG. 1, valves 6a, 8a are open and a valve 6b is closed, and all of the amount of powder and granular material P flowing in the line 2 flows into piping 2a and through the cell 7 connected to piping 2a. That is, under the illustrated condition, the light transmission type powder and granular material measuring apparatus 1 can accurately measure the concentration and particle size distribution of the powder and granular material P flowing in line 2. Continuing the measurement causes the powder and granular material P to gradually adhere to the inner wall surface, including the portions of glass windows 7a, 7b of the cell 7, and it is unavoidable that the powder and granular material P adhering to these glass windows 7a, 7b causes errors to be included in the measurement value of the light transmission type powder and granular measuring apparatus 1.

Therefore, with proper intervals provided, it is necessary to carry out a calibrating blank or reference measurement for correcting the errors caused by the powder and granular material P adhering to the glass windows 7a, 7b. When this blank measurement is carried out, in the light transmission type powder and granular measuring apparatus 1 of this example, the valves 6a, 8a are closed and simultaneously the valve 6b is opened to completely stop the flow of the powder and granular material P for the piping 2a, and at the same time, the flow of the powder and granular material P on the line 2 can be continued by the other piping 2b.

Consequently, without affecting the operation of line 2, since the supply of powder and granular material P for the cell 7 can be completely stopped, a blank measurement of the cell 7 can be carried out without stopping the tablet compression molding machine 4. In this example, valves 6a, 8a are mounted on both the upstream side and the downstream side of the cell 7, and even if the cell 7 is removed from the piping 2a, no obstacle is generated in the flow of the line 2. Consequently, it is possible to carry out maintenance or even replace the cell 7 as required by removing the cell 7 without shutting down the plant. This invention is not limited to mounting the valve 6b at the downstream side of the cell, that is, the confluence point B of the piping 2a, 2b.

A system controller 12, such as a programmed microprocessor, can automatically open and close valve members and enable the measurements of the blank or reference measurements and the production flow measurements. Thus, a calibration cycle can be automatically programmed into the system controller 12, and it can act as the host computer to a slave controller, such as controller 9.

As described above, when processing such as the blank measurement of the cell 7 is completed, the light transmission type powder and granular material measuring apparatus 1 can accurately measure the concentration and particle size distribution of the powder and granular material P in the line 2 by bringing the valves 6a, 8a into the open condition again, and the valve 6b into the closed condition.

Figure 3:
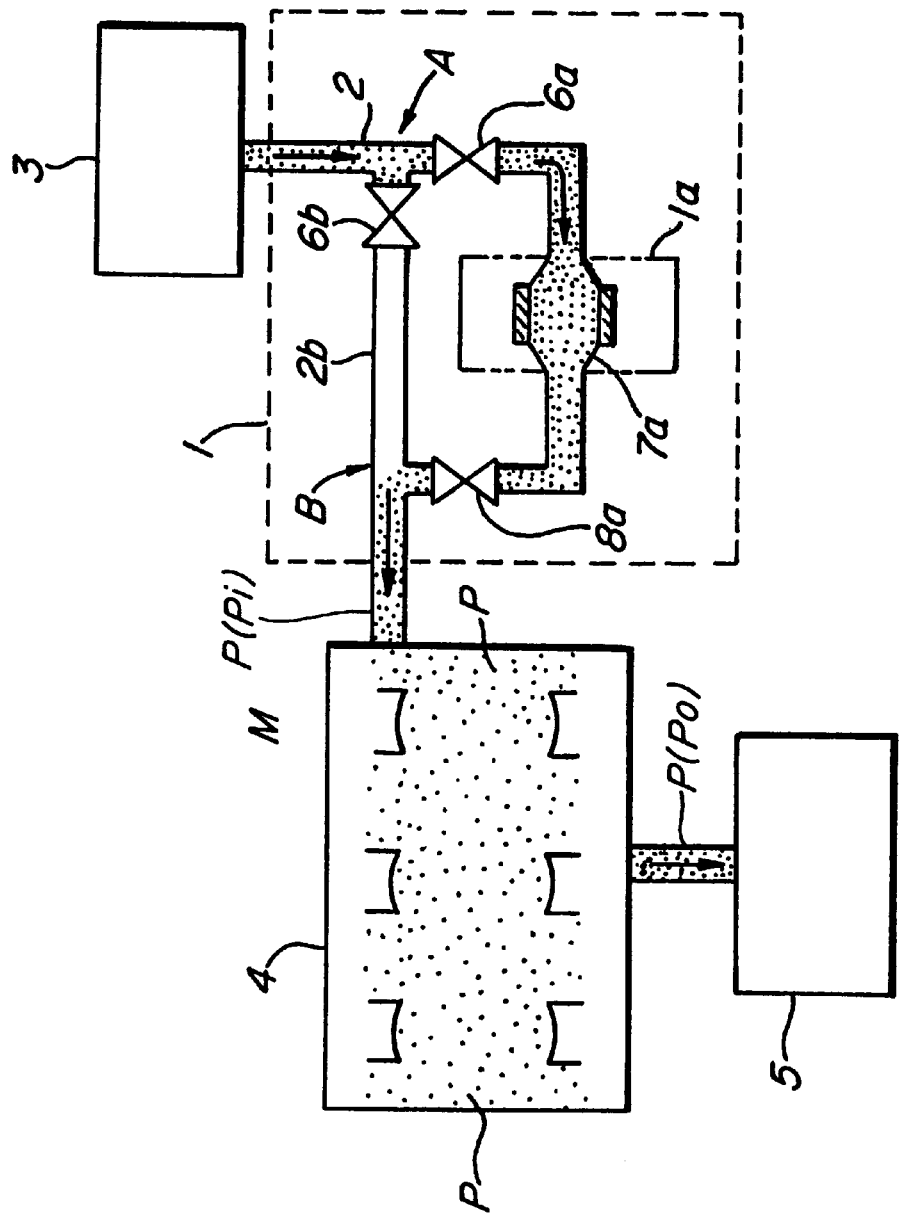
FIG. 3 is a drawing showing another example of using a light transmission type powder and granular material measuring apparatus in a production plant line.

In the above example, the light transmission type powder and granular material measuring apparatus 1 is located on the downstream side of the tablet compression molding machine 4, but as shown in FIG. 3, by locating the light transmission type powder and granular material measuring apparatus 1 on the upstream side of the tablet compression molding machine 4, it is possible to measure the concentration and particle size distribution of the powder and granular material Pi supplied to the tablet compression molding machine 4. In addition, by installing the light transmission type powder and granular material measuring apparatus at both the upstream and downstream sections of the tablet compression molding machine 4, the consumption rate of the powder and granular material P at the tablet compression molding machine 4 can be accurately computed with time, and product quality control can be carried out accurately. Other operations are the same as in FIG. 1 and FIG. 2, and a detailed description will be omitted.

Figure 4:
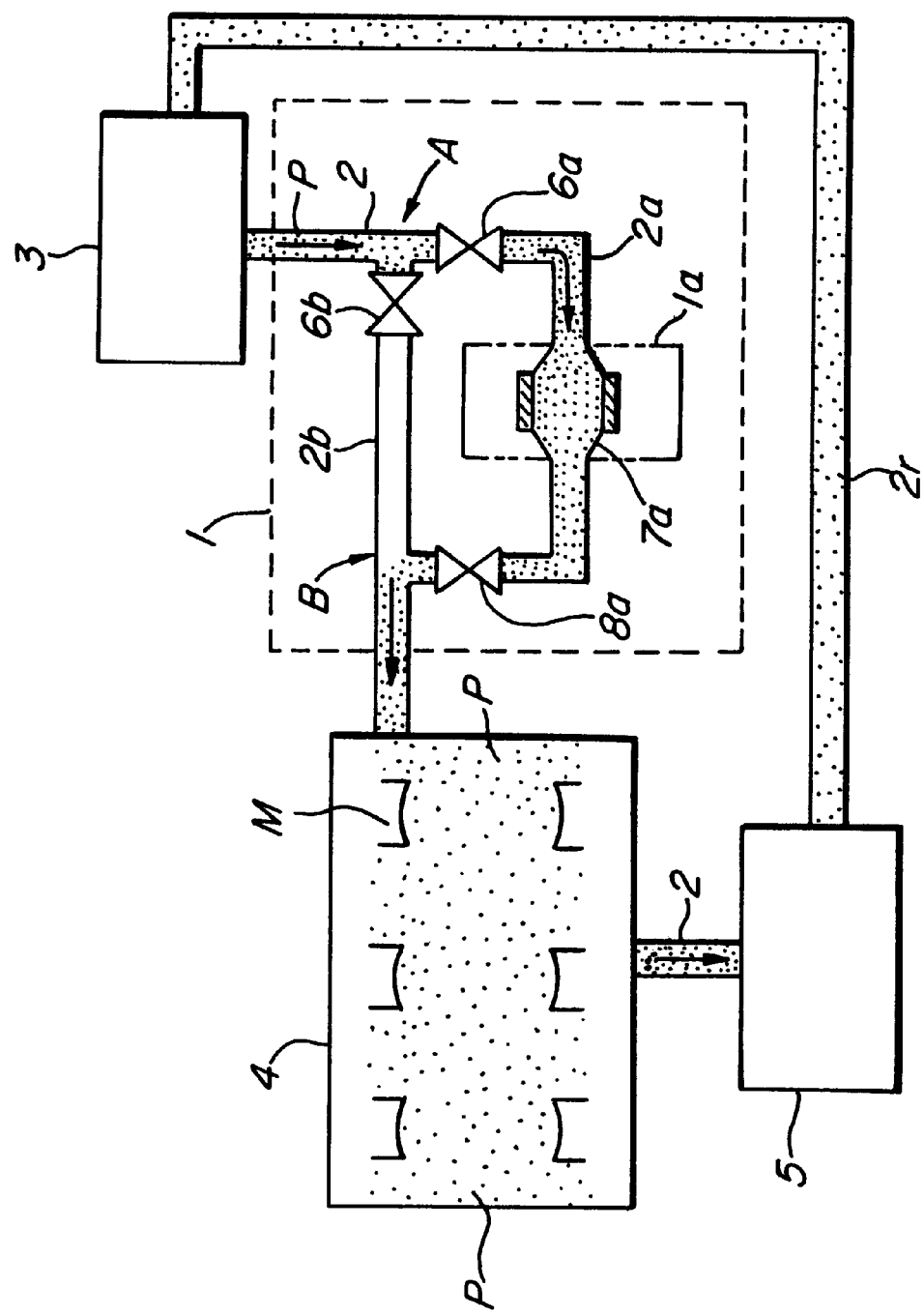
FIG. 4 is a drawing showing a variation of the apparatus shown in FIG. 3.

FIG. 4 shows another example in which the powder and granular material P sucked by the aspirator 5 is returned to the powder and granular transporting apparatus 3 by the other piping 2r. By configuring in this way, the powder and granular material P in line 2 is allowed to flow at a specified amount without wasting the powder and granular material P as well as without requiring extra effort. Other points are the same as in FIGS. 1–3, and a detailed description will be omitted.

Figure 5:
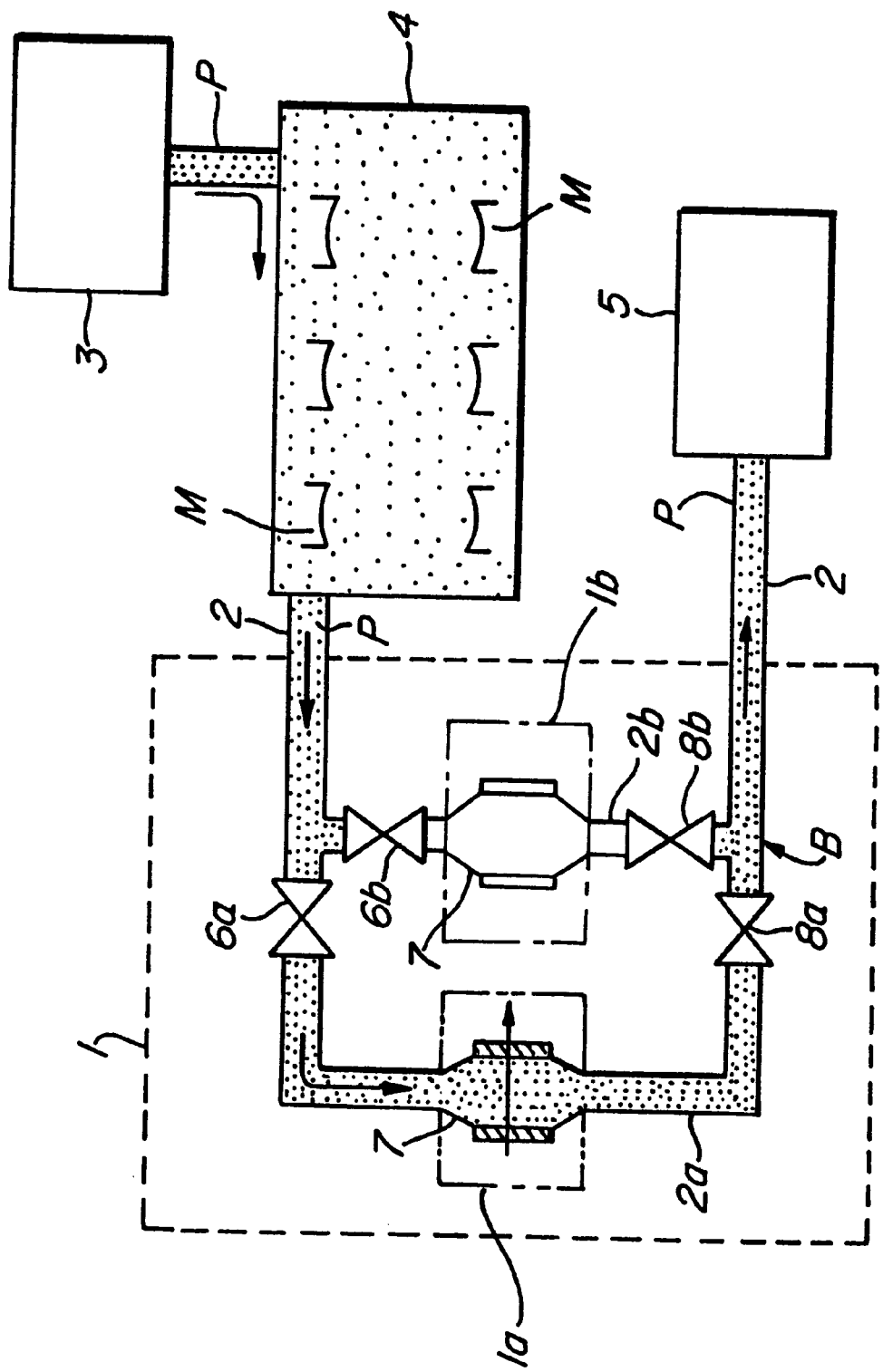
FIG. 5 is a drawing showing another example of a light transmission type powder and granular material measuring apparatus according to this invention.

FIG. 5 shows still another example of a light transmission type powder and granular material measuring apparatus 1 according to this invention. What differs from the light transmission type powder and granular measuring apparatus 1 of FIGS. 1–4, is that this light transmission type powder and granular material measuring apparatus 1 has optical chambers 1a, 1b equipped in each of the two branched piping 2a, 2b, respectively, and as a result, a valve 8b is equipped on the downstream side of the optical chamber 1b.

By configuring in this manner, while the optical chamber 1a is carrying out a blank measurement, etc., it is possible to measure the powder and granular material P flowing in line 2 using the optical chamber 1b, and conversely, while the optical chamber 1b is carrying out a blank measurement, etc., it is possible to measure the powder and granular material P flowing in line 2 using the optical chamber 1a. That is, because the concentration and particle size distribution of the powder and granular material P running in line 2 can be continuously measured, it is possible to properly carry out quality control of the product manufactured using line 2. Needless to say, the valves 8a, 8b may be substituted with a three-way valve mounted at the confluence point B. Other operation features may also be changed in the same manner as in the example shown in FIGS. 1–4.

In addition, in each of the examples, a line 2 in a pharmaceutical plant for generating granular chemicals is illustrated as an example of a plant line using a light transmission type powder and granular material measuring apparatus 1 according to this invention for convenience, but this invention is not limited to this example and can be used for any lines which are lines for conveying powder and granular material. Because the powder and granular material can be measured without stopping the flow of the powder and granular material on the line, as shown in each of the examples described above, the light transmission type powder and granular measuring apparatus according to this invention can be connected as a modular unit to a general plant line. As described above, according to this invention, the entire amount of the powder and granular material flowing on the line can be allowed to flow in a separate branched piping by switching valves. That is, because it is possible to carry out a blank measurement of the cell measured by the light transmission type powder and granular measuring apparatus while the powder and granular material can be allowed to flow in the other piping, a plant using this line can continuously and constantly be operated without stopping the powder and granular material flowing in the line. Consequently, even in a plant line which is unable to stop the line flow, the light transmission type powder and granular material measuring apparatus can be directly installed and processing of still higher accuracy can be achieved.

When a valve is installed in the space from the confluence point to the cell, removing the cell from the piping for maintenance with the valve changed over to prevent the powder and granular material from flowing into the cell can further improve the accuracy of the light transmission type powder and granular measuring apparatus. In addition, when a light transmission type cell is mounted to both of the two pieces of piping, respectively, the measurement of the concentration and particle size distribution of the powder and granular material can continuously be carried out with the one cell, while the other cell is subject to a blank measurement or being maintained, thereby enabling constant and accurate measurement of the powder and granular material flowing on the plant line.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. A light transmission type powder and granular measuring apparatus, comprising:

two pieces of piping connected in such a manner as to branch a powder and granular material flowing line into two directions at a divergence point and to join again at a confluence point;

a valve which is installed at the divergence point and can be changed over to allow the powder and granular material to selectively flow in either one of the piping pieces; and a light transmission type cell mounted to the midway of at least one of the piping pieces, wherein both the condition in which the powder and granular material is allowed to flow in the cell and the condition in which the powder and granular material is not allowed to flow in the cell can be measured by changing over the valve without stopping the flow of the powder and granular material.

2. A light type powder and granular measuring apparatus according to claim 1, wherein a valve is mounted adjacent the confluence point to the cell.

3. A light transmission type powder and granular material measuring apparatus according to claim 2, wherein a light transmission type cell is mounted in each one of the pieces of piping, respectively.

4. A light transmission type powder and granular material measuring apparatus according to claim 1, wherein a light transmission type cell is mounted in each one of the pieces of piping, respectively.

5. A light transmission powder and granular measuring apparatus for a continuous production line assembly having a first conduit that transmits powder and/or granular material comprising:

a second conduit connected to the first conduit;

a first light transmission cell mounted in the second conduit;

a first measuring apparatus for measuring light as it passes through the first light transmission cell; and a first valve member interconnecting the first and second conduit to control the flow of powder and/or granular material through the second conduit, whereby a measurement of the powder and/or granular material can be made when the valve member is activated to permit the flow of powder and/or granular material through the second conduit and a reference measurement can be made when the valve member is activated to stop the flow of powder and/or granular material.

6. A light transmission powder and granular measuring apparatus as in claim 5, further including a third conduit connected to the first conduit, a second light transmission cell mounted in the third conduit, a second measuring apparatus for measuring light as it passes through the second light transmission cell, and a second valve member interconnecting the first conduit and the third conduit to control the flow of powder and/or granular material through the third conduit, whereby a measurement of the powder and/or granular material can be made in either the first or second light transmission cell, while a reference measurement can be made in the other of the first or second light transmission cell.

7. A light transmission powder and granular measuring apparatus as in claim 5, further including a system controller for activating the first valve member to interconnect the second conduit and to enable the first measuring apparatus for measuring light and for deactivating the first valve member to disconnect the second conduit and to enable the first measuring apparatus to measure a reference value.

8. A system for calibrating and measuring a flow of powder and/or granular material in a constant flow production line having a first conduit that transmits powder and/or granular material, comprising:

a second conduit controllably connected to the production line and capable of transmitting the flow of powder and/or granular material along an alternative path;

a first light transmission cell mounted in the second conduit;

a first measuring apparatus for measuring light as it passes through the first light transmission cell;

a first valve member interconnecting the first and second conduit to control the flow of powder and/or granular material through the second conduit; and a system controller connected to the first valve member and the first measuring apparatus for activating the first valve member to interconnect the second conduit to transmit the flow of powder and/or granular material and enabling the first measuring apparatus for measuring light and for deactivating the first valve member to disconnect the second conduit and to enable the first measuring apparatus to measure a reference value.

* * * * *